United States Patent [19]

Matteson

[11] Patent Number: 4,569,226
[45] Date of Patent: Feb. 11, 1986

[54] AUTOMATED INTERFACIAL TENSIOMETER

[75] Inventor: Michael J. Matteson, Decatur, Ga.

[73] Assignee: Georgia Tech. Research Institute, Atlanta, Ga.

[21] Appl. No.: 606,289

[22] Filed: May 2, 1984

[51] Int. Cl.$^4$ ............................................. G01N 13/02
[52] U.S. Cl. ..................................... 73/64.4; 324/71.4
[58] Field of Search ............... 73/64.4; 324/71.1, 71.4, 324/452, 453, 457, 458, 61 R; 377/10

[56] References Cited

U.S. PATENT DOCUMENTS

| B 351,735 | 1/1975 | Jobe | 73/64.4 |
|---|---|---|---|
| 2,756,388 | 7/1956 | McLean | 324/453 |
| 3,124,172 | 3/1964 | Paxson, Jr. | 324/453 |
| 3,836,912 | 9/1974 | Ghougasian et al. | 324/71.4 |
| 4,196,615 | 4/1980 | Davis | 73/64.4 |

FOREIGN PATENT DOCUMENTS 601602  4/1978  U.S.S.R. ............................. 73/64.4

OTHER PUBLICATIONS

Titcomb, Instrument for Measuring Dynamic Surface Tension, IBM Technical Bulletin, 1979.

Primary Examiner—Stewart J. Levy
Assistant Examiner—Hezron E. Williams
Attorney, Agent, or Firm—Newton, Hopkins & Ormsby

[57] ABSTRACT

The interfacial tension in a liquid-liquid system is determined by estimating the flow rate of the heavier liquid as it is discharged under constant head through a capillary immersed in a body of the lighter liquid. A known voltage is applied to each drop which forms at and detaches from the capillary tip and an electrometer is used to measure the total electrical charge per drop and the frequency of drop formation/detachment. The determination is made under conditions in which a plot of interfacial tension versus the square of the applied voltages yields two straight lines whose slopes of $\pm C/2$ where C is the capacitance of the interface per unit area and the positive value is generated from the positive polarity voltage and the negative from the negative polarity. Based upon the value of C determined from the slope, the known voltage and the measured values of dropping frequency and of total charge per drop, the correctness of the estimated flow rate is determined and, in an iterative process, a new flow rate estimation and consequent plots are made until the estimated flow rate equals the flow rate as determined from measurements. The value of the interfacial tension at zero charge is then obtained from the intersection of the two lines.

3 Claims, 3 Drawing Figures

AUTOMATED INTERFACIAL TENSIOMETER

BACKGROUND OF THE INVENTION

There are a number of techniques for the purpose of determining interfacial tension in a liquid-liquid systems. The Jobe Pat. No. 3,913,385 and corresponding published patent application No. B 351,735 employs a continuous type monitor for hydrocarbon liquids for automatically detecting the presence of a surface active agent in the hydrocarbon liquid, and employs a caustic liquid to form drops in the monitored liquid. The Davis Pat. No. 4,196,615 employs a tensiometer which measures changes in capacitance between monitored plates as effected by passage of drops of one liquid falling through a body of a second liquid. The Jobe Pat. No. 3,881,344 measures surface tension of a stream of flowing liquid as a function of the pressure required to form an air bubble below the surface of the liquid. The Jennings, Jr. et al Pat. No. 3,483,737 employs apparatus for measuring interfacial tension by the pendant drop method. The Russian reference No. SU-601,602 (Sakalskii) employs an instrument in which high voltage is used to break up the surface of a liquid, the voltage value at that time being a measure of the surface tension.

Many methods involve withdrawing a sample, preparing for analysis and then making measurement of interfacial tension according to:

(a) pendant drop method—in which one liquid is allowed to grow slowly from a capillary immersed in a second liquid. Either the detached drop is weighed or a photograph is made and an analysis is performed on the shape.

(b) ring method—a ring is immersed to the level of the interface and the ring is slowly pulled out of the interfacial region and the force measured.

(c) spinning drop method—a drop of the lighter liquid is placed in a capillary between columns of the heavier liquid and rotated about the axis; and analysis of the contact angle is made.

BRIEF SUMMARY OF THE INVENTION

In many industrial processes it is desirable to be able to measure interfacial tension between two liquids or between two liquids with a surface active agent adsorbed at the interface. The present invention is directed to novel apparatus and method of measuring interfacial tension in a liquid-liquid system and in particular to a technique which lends itself to providing an automated, on-line tensiometer capable of measuring and recording or otherwise reporting interfacial tension before material is introduced into a process. Quality control or other types of monitoring functions are obviously possible. The technique has the capability of:

(a) instantaneous response
(b) on-line measurement
(c) direct read-out of interfacial tension
(d) detection of trace amounts of surfactants According to the invention, a constant head is applied to a heavier liquid as it is discharged through the tip of a capillary immersed in a body of the lighter liquid. A pool of the heavier liquid is formed within the body of lighter liquid in spaced relation below the capillary tip and a known but variable d.c. voltage is maintained between the heavier liquid drop and this pool. Under these circumstances, the interfacial tension $\gamma$ between the liquids is related to the electrical charge Q per unit area of a drop and the applied voltage V according to the following:

$$\gamma = \gamma_o^{\frac{1}{2}} Q V \tag{1}$$

where $\gamma_o$ is the interfacial tension in the absence of electrical charge and is, hence, the value of interest.

If C, the capacitance of the interface per unit area, is constant over a range of voltages V, then $Q = CV$ and equation (1) may be expressed as:

$$\gamma = \gamma_o^{\frac{1}{2}} C V^2 \tag{2}$$

Since equation (2) is of the classical straight line form $y = mx + b$ where $y = \gamma$, $x = V^2$, m is the slope equal to $C/2$ and b is $\gamma_o$, it demonstrates that if $\gamma$ is plotted versus $V^2$, such a plot will be a straight line which intercepts the ordinate at b, the value of $\gamma$ equal to $\gamma_o$.

However, the values of $\gamma$ and C are both unknown and the desired plot cannot be made on the basis of equation (2).

The relation between interfacial tension, $\gamma_o$, and liquid flow rate, q, has been developed by Scheele and Meister* for droplet formation at low flow rates. These authors present a force balance on the suspended droplet wherein the terms $$\text{Vol } g\Delta\rho = \psi_H \left[ \pi\gamma d_{oro} + \frac{13\mu q d_{ori}}{\text{Vol}^{\frac{1}{3}}} - \frac{16\rho_p q^2}{3\pi d_{ori}^2} + \frac{9}{2} \{g\rho_p \Delta\rho\gamma d_{ori}^2 q^2\}^{\frac{1}{3}} \right]$$

represents the gravitational force, interfacial tension, Stokes' drag, momentum, and volume added during necking.
*AIChE J., 14, 9–19 (1968).

The Stokes' drag term is negligible in these types of measurements, so the above equation may be rearranged in more explicit form for interfacial tension $$\gamma + E\gamma^{\frac{1}{3}} - F/f - G = 0 \tag{3}$$

where E, F and G are constants and f is the frequency of drop formation/detachment, $$f = \frac{q}{\text{Vol}} \text{ and}$$

$$E = \frac{\frac{9}{2} [g\rho_p \Delta\rho d_{ori}^2 q^2]^{\frac{1}{3}}}{\pi d_{oro}}$$

$$F = \frac{qg\Delta\rho}{\psi_H \pi d_{oro}}$$

$$G = \frac{16\rho_p q^2}{3\pi^2 d_{ori}^2 d_{oro}}$$

where
g = gravitational acceleration
$\rho_p$ = density of heavier fluid
$\Delta\rho$ = difference in density between heavier and lighter fluids
$d_{ori}$ = inner orifice diameter of capillary
$d_{oro}$ = outer orifice diameter of capillary $\psi_H$ = Harkins correction factor for drop attachment $$= 1.00 - 0.660 \left( \frac{d_{orif}}{q^{\frac{1}{3}}} \right) + 0.339 \left( \frac{d_{orif}}{q^{\frac{1}{3}}} \right)^2 \quad 5$$

A plot of $\gamma$ versus $V^2$ based upon equation (3) will yield an accurate determination of $\gamma_o$ to the extent that an accurate approximation of q has been made and f has been accurately measured. The question, then, is to check the accuracy of the estimated value of q and, if incorrect, to adjust it and repeat the plot according to equation (3) and check the new estimated value of q until the correct value of q is found. At that time, the ordinate intercept of the plot yields the correct value of $\gamma_o$. However, it is preferred for accuracy to make two plots from equation (3), one in which $V^2$ vs. $\gamma$ is generated from a positive polarity and has a positive slope, and the other in which $V^2$ vs. $\gamma$ is generated from a negative polarity and has a negative slope. This generates two straight lines which intersect at $Y_o$, which may not necessarily occur at $V^2=0$.

In order to check the estimated value of q, the slope of the plot is determined which, from equation (2), equals $\frac{1}{2}$ C. This value of C is used in equation (6) here following to check the accuracy of the estimation of q.

The volume of an individual drop is:

$$\text{Vol} = \frac{S^{3/2}}{6\pi^{\frac{1}{2}}} \quad (4)$$

where S is the surface area per drop. Since, by definition, the total charge QT per drop equals QS, and since Q=CV, equation (4) may be expressed:

$$\text{Vol} = \frac{1}{6\pi^{\frac{1}{2}}} \left[ \frac{Q_T}{CV} \right]^{3/2} \quad (5)$$

Since the actual flow rate equals fVol, the estimated flow rate used in equation (3) can be checked for accuracy from measured values of V,f and $Q_T$ and the value of C determined from the slope of equation (2). Thus, using the symbol q' to distinguish from the estimated flow rate q and using equation (5):

$$q' = f \text{Vol} = \frac{f}{6\pi^{\frac{1}{2}}} \left[ \frac{Q_T}{CV} \right]^{3/2} \quad (6)$$

Thus, if f and $Q_T$ are measured and the value of C determined from the slope of the equation (2) plot the accuracy of the estimated value of q may be checked.

The values of V, $Q_T$ and f may be measured by suitable electronic apparatus and if the solution of equation (6) indicates that the estimated value of q used in equation (3) was in error, i.e., q≠q', a new value of q is used to form a new plot. This iterative process yields results which display an accuracy of at least 0.60% in the measurement of interfacial tension.

BRIEF DESCRIPTION OF THE DRAWING FIGURES

DETAILED DESCRIPTION OF THE INVENTION

Figure 1:
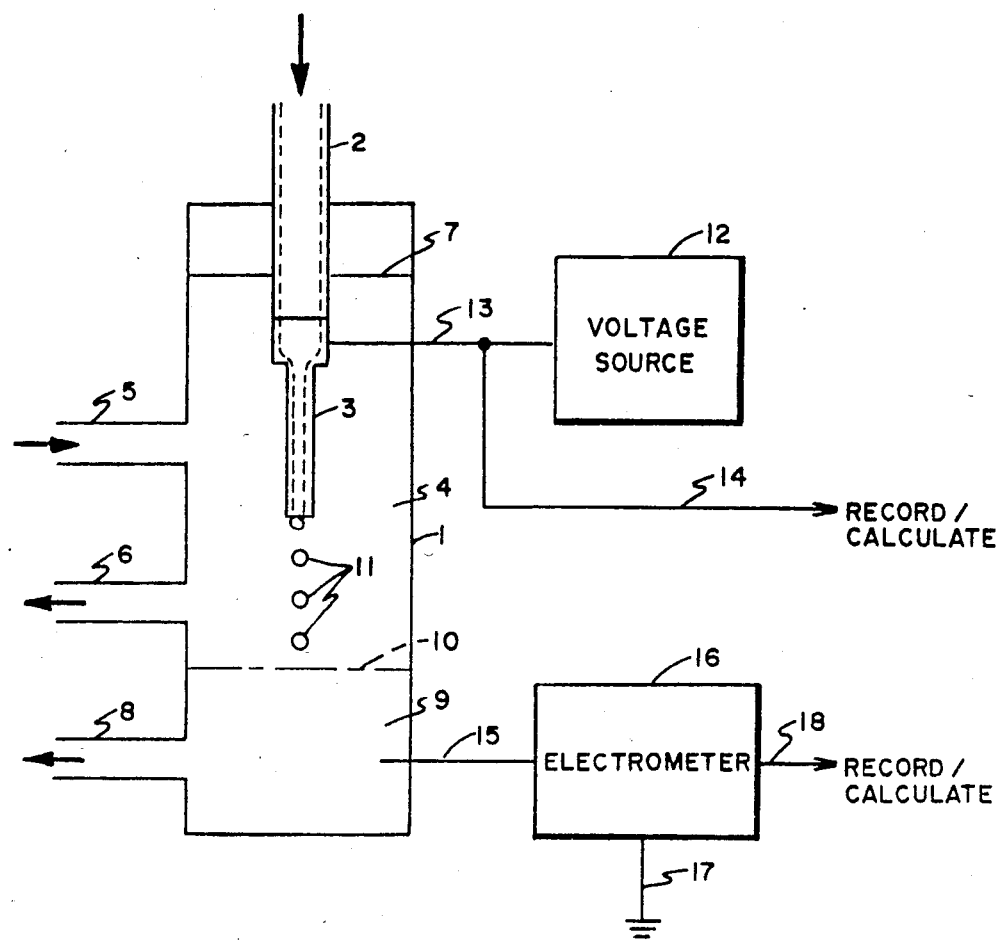
FIG. 1 is a schematic representation of one form of the invention.

FIG. 1 is a simplified diagram of a system according to the invention. The vessel or cell 1 is provided with an inlet line 2 for the heavier liquid supplied from any suitable constant head source and, within the vessel, the heavier liquid is discharged through the capillary 3 into a body 4 of the lighter liquid. The lighter liquid is introduced into the vessel through the inlet line 5 and is drained through the outlet line 6. The line 5 is connected to any suitable constant head source for the lighter liquid and the body 4 is maintained at the fixed height within the vessel as is indicated by the reference character 7. Likewise, the heavier liquid is drained at the outlet line 8 so that, as supplied by the constant head source of heavier liquid through the capillary 3, a pool 9 of the heavier liquid is maintained whose interface 10 with the body 4 of lighter liquid is maintained at a fixed level well below the tip of the capillary 3, i.e, large enough that the flow rate of the heavier liquid is unaffected by the electrical charge imparted to the drops 11 of the heavier liquid.

The capillary 3 is metallic and is connected to the voltage source 12 by the conductor 13 which is also connected as at 14 to suitable instrumentalities for recordation and calculation. The voltage source is variable and capable of delivering between 0 and 2000 volts of either polarity. The pool 9 of the heavier liquid is grounded through the conductor 15 and the electrometer 16 to the ground connection 17 and the output conductor 18 of the electrometer is connected to the instrumentalities for recordation and calculation. The electrometer is capable of registering the frequency f of charge pulses generated by the droplets striking the pool of heavier liquid. It is also capable of measuring the flow of current delivered over a certain time and integrating this quantity to obtain $$Q_T = \int_0^t i \, dt$$

Figure 2:
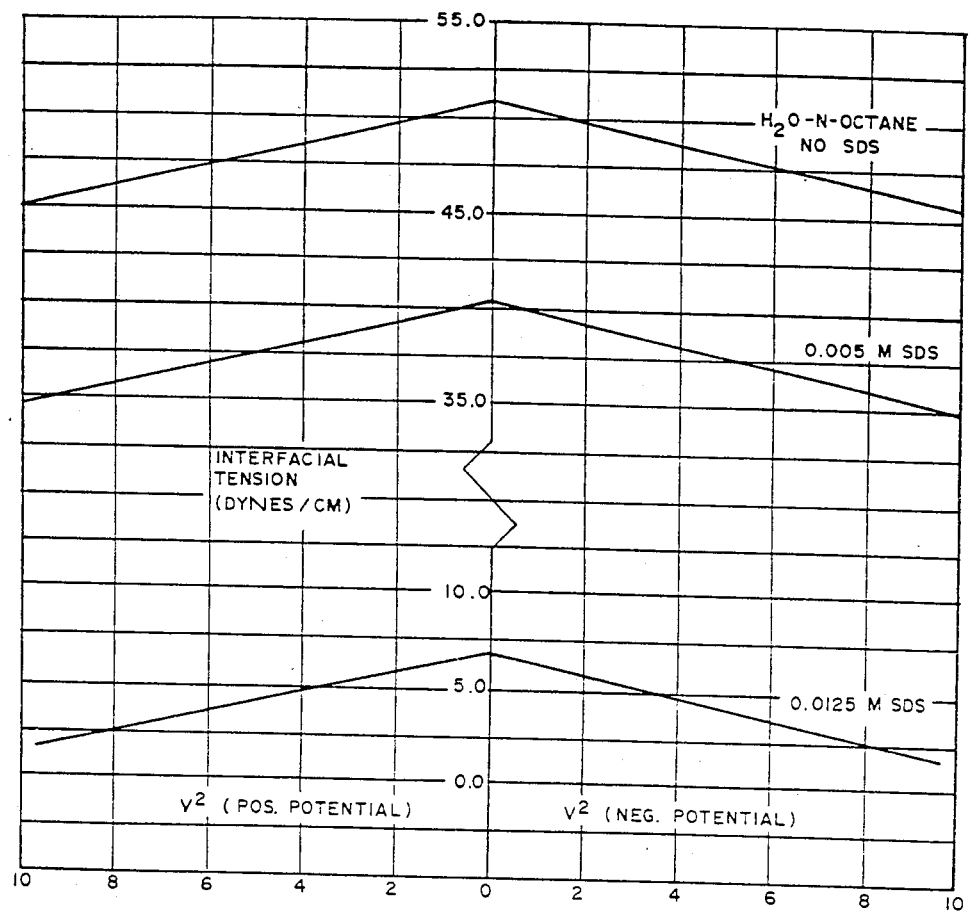
FIG. 2 illustrates curves for the water-n-octane system with and without a surfactant added.

As noted earlier, the flow rate of the heavier liquid is unaffected by the voltage supplied by the source 12 but the size of the drops 11 which form at and detach from the capillary is affected. Thus, the size of the drops and the frequency of drop formation/detachment is a function of the voltage. The electrometer 16 is used to measure the frequency f and the total charge $Q_T$ per drop for various values of V as measured from the voltage source 12. The estimated value q, the voltage V and the measured frequency f are used to calculate the values of the $\gamma$ vs $V^2$ plots according to equation (3). At the same time, the values of f and $Q_T$ and corresponding levels of voltage V are employed to calculate the value of q' from equation (6). Typical $\gamma$ vs $V^2$ lots are shown in FIG. 2, from which the slope C/2 is determined for use in equation (6) to complete the determination of q'. As noted before, an iterative process is used until q=q', at which time the desired value $Y_o$ is determined. FIG. 2 shows data for the water-n-octane system, and also for that same system with a surfactant, sodium dodecyl sulfate, added. Results of ten different concentrations of surfactant are presented in Table 1. These results show that for the pure system, without surfactant, the intersection of the two lines yields a value of 50.8 dynes cm$^{-1}$, with a correlation coefficient of 0.991 for the positive polarity and 0.999 for the negative polarity. The accepted value for the interfacial tension at 20° C. is 50.8 dynes cm$^{-1}$. The interfacial capacitance, obtained from rhe slopes of the $\gamma$ vs V$^2$ curves, and the interfacial tensions obtained from the intersections of the lines, for ten different concentrations show that the capacitance is independent of the surfactant concentration and only slightly greater (1.088 vs. 1.078 statfarads cm$^{-2}$) for the negative polarity when compared with the positive.

TABLE 1

Characteristics of Interfacial Tension vs Voltage$^2$ Plot at Several Surfactant Concentrations.

| Concentration SDS moles l$^{-1}$ | Interfacial Tension at Zero Charge $\gamma_o$, dynes cm$^{-1}$ | Interfacial Capacitance Statfarads cm$^{-2}$ Polarity | | Correlation Coefficient Polarity | |
|---|---|---|---|---|---|
| | | (+) | (−) | (+) | (−) |
| 0.00 | 50.8 | 1.084 | 1.128 | 0.991 | 0.999 |
| 2.50 × 10$^{-4}$ | 44.6 | 1.034 | 1.124 | 0.974 | 0.989 |
| 5.00 × 10$^{-4}$ | 40.2 | 1.122 | 1.094 | 0.994 | 0.998 |
| 1.00 × 10$^{-3}$ | 33.7 | 1.162 | 1.150 | 0.983 | 0.998 |
| 3.00 × 10$^{-3}$ | 22.4 | 1.372 | 1.118 | 0.993 | 0.993 |
| 4.00 × 10$^{-3}$ | 17.5 | 1.166 | 1.040 | 0.950 | 0.997 |
| 6.25 × 10$^{-3}$ | 8.85 | 1.082 | 1.112 | 0.993 | 0.983 |
| 1.25 × 10$^{-2}$ | 6.72 | 0.884 | 1.010 | 0.994 | 0.982 |
| 2.50 × 10$^{-2}$ | 6.30 | 0.848 | 0.938 | 0.998 | 0.980 |
| 5.00 × 10$^{-2}$ | 6.71 | 1.028 | 1.166 | 0.991 | 0.993 |
| | | C$_+$ = 1.078 | C$_-$ = 1.088 | | |
| | | $\sigma_{n+}$ = 0.14 | $\sigma_{n-}$ = 0.0672 | | |

Figure 3:
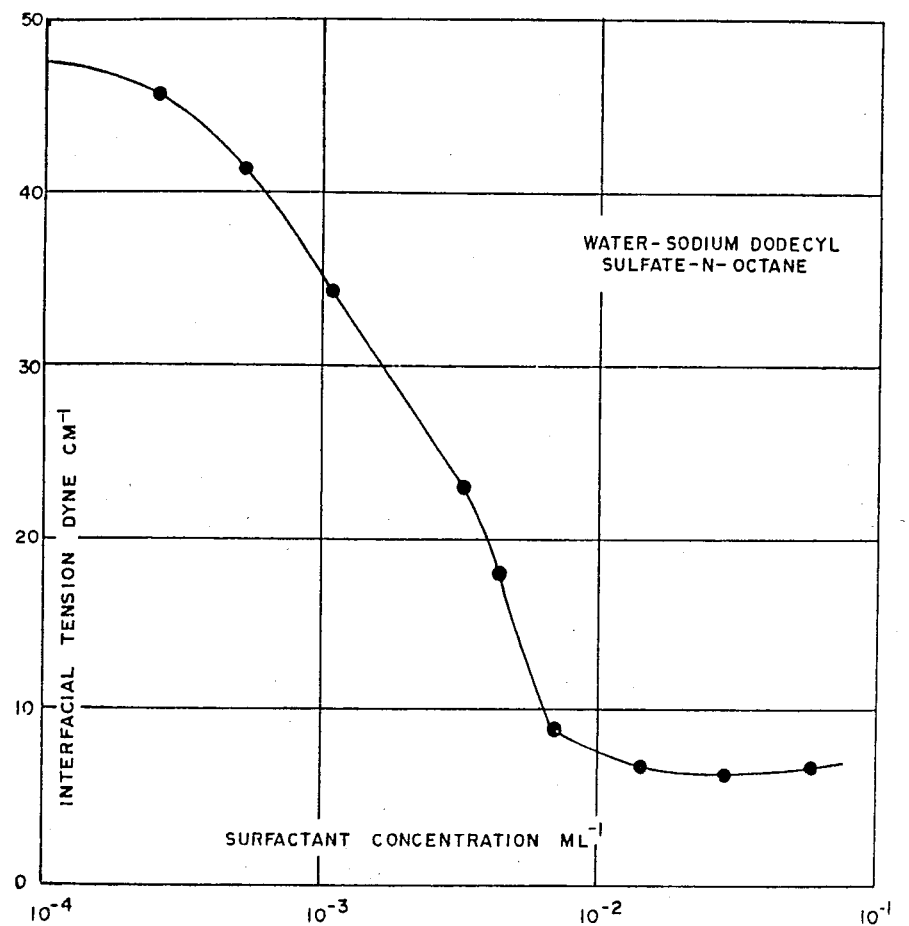
FIG. 3 is a curve generated by successive dilutions to determine the presence and amount of surfactant.

FIG. 3 is a plot of the values of $\gamma_o$ at the various surfactant concentrations vs the log of the surfactant concentration C'. From the slope of this curve $$\frac{d\gamma_o}{d\ln C'} = -kT\Gamma_o$$

one is able to obtain $\Gamma_o$ the amount of surfactant adsorbed at the interface; k is Boltzmann's constant and T is temperature. This data is presented in Table 2.

TABLE 2

Adsorption of Sodium Dodecyl Sulfate at Water-n-Octane Interface.

| Concentration SDS moles l$^{-1}$ | Interfacial Tension $\gamma_o$, dynes cm$^{-1}$ | $\dfrac{-d\gamma_o}{d\ln C}$ dynes cm$^{-1}$ | Adsorption at Interface $\Gamma_o$, $\dfrac{\text{molecules}}{\text{nm}^2}$ |
|---|---|---|---|
| 0.00 | 50.8 | 0 | 0 |
| 2.50 × 10$^{-4}$ | 44.6 | 1.97 | 0.479 |
| 5.00 × 10$^{-4}$ | 40.2 | 6.14 | 1.49 |
| 1.00 × 10$^{-3}$ | 33.7 | 9.86 | 2.40 |
| 3.00 × 10$^{-3}$ | 22.4 | 9.86 | 2.40 |
| 4.00 × 10$^{-3}$ | 17.48 | 20.0 | 4.86 |
| 6.25 × 10$^{-3}$ | 8.85 | 20.0 | 4.86 |
| 1.25 × 10$^{-2}$ | 6.72 | 3.26 | 0.792 |
| 2.50 × 10$^{-2}$ | 6.30 | 0.782 | 0.190 |
| 5.00 × 10$^{-2}$ | 6.71 | −0.826 | −0.201 |

This information is obtained from the invention by making a measurement of $\gamma_o$ at the concentration of the unknown surfactant in the system. Then by making successive dilutions of the unknown surfactant in the system by successively diluting the system by additions of constant amounts of the pure liquid of the system, and measuring $\gamma_o$ at each dilution, one is able to generate a curve similar to that of FIG. 3. If C$_1$' is the original unknown concentration of surfactant and the liquid containing this unknown concentration is mixed with an equal amount of pure liquid to yield a new system of diluted concentration C$_2$', then $$\Delta \ln C' = \ln C_1' - \ln C_2' = \ln \frac{C_1'}{C_2'}$$

$$\ln \frac{C_1}{C_2} = \ln 2.0 = 0.693$$

Now if $\gamma_o$ is measured at these two concentrations C$_1$' and C$_2$':

$$\frac{\Delta \gamma_o}{\Delta \ln C'} = \frac{\gamma 01 - \gamma 02}{0.693} = -kT\Gamma_o$$

The dilution factor ½ is used here as an example only, and in actual cases the dilution could be on the order of 0.8–0.9.

The presence and amount of surface active agent is then easily determined.

The invention has a number of advantages:
(a) The response at each voltage is almost instantaneous. Therefore, an electronic instrument can scan the voltages, measure the corresponding frequencies and determine the intersection of the two polarity lines in a few seconds.
(b) Liquids can be continuously fed into and out of the cell or vessel so that on-line measurements may be made.
(c) Direct read-out of interfacial tension is obtained.
(d) Even trace amounts of impurities which are surface active are rapidly detected.

What is claimed is:
1. The method of determining the interfacial tension in a liquid-liquid system in which one liquid has a greater density than the other, which comprises the steps of:
(a) forming a body of said other liquid which is of lesser density;
(b) introducing said one liquid which is of greater density dropwise into the other liquid at a rate which may be estimated;
(c) imparting a total electrical charge Q$_T$ on each drop of the one liquid by the application of voltage V and varying such voltage so that some drops carry charges which are different from the charges of other drops;
(d) measuring the frequency f of the drops and the total electrical charge Q$_T$ carried by each drop;
(e) determining the values of the interfacial tension $\gamma$ for different V and measured f and plotting $\gamma$ vs V$^2$ therefrom;
(f) determining the value of the capacitance C per unit area per drop from the slope of the plot of step (e) and calculating the value of actual flow rate q' based upon the value of C, f, V and Q$_T$; and
(g) repeating steps (a)–(e) until the estimated liquid flow rate of step (b) equals q'.
2. The method as defined in claim 1 wherein the heavier and lighter liquids are continuously introduced into and withdrawm from a common vessel.
3. The method as defined in claim 2 wherein each liquid is introduced into the common vessel at a respective constant head.

* * * * *